US006712752B2

(12) United States Patent
Slater et al.

(10) Patent No.: US 6,712,752 B2
(45) Date of Patent: *Mar. 30, 2004

(54) RADIOACTIVE THERAPEUTIC SEED HAVING SELECTIVE MARKER CONFIGURATION

(75) Inventors: Charles R. Slater, Fort Lauderdale, FL (US); Thomas O. Bales, Coral Gables, FL (US)

(73) Assignee: Syntheon, LLC, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/295,658

(22) Filed: Nov. 15, 2002

(65) Prior Publication Data

US 2003/0092959 A1 May 15, 2003

Related U.S. Application Data

(63) Continuation of application No. 09/514,787, filed on Feb. 28, 2000, now Pat. No. 6,482,143, and a continuation-in-part of application No. 09/371,243, filed on Aug. 10, 1999.

(51) Int. Cl.[7] ............................................... A61N 5/00
(52) U.S. Cl. ............................................................. 600/8
(58) Field of Search ................................ 600/1–8, 427; 128/898; 29/592; 378/20

(56) References Cited

U.S. PATENT DOCUMENTS

| 3,351,049 A | 11/1967 | Lawrence | 128/1.2 |
| 4,323,055 A | 4/1982 | Kubiatowicz | 128/1.2 |
| 4,702,228 A | 10/1987 | Russell, Jr. et al. | 128/1.2 |
| 4,784,116 A | 11/1988 | Russell, Jr. et al. | 128/1.2 |
| 4,891,165 A | 1/1990 | Suthanthiran | 252/633 |
| 5,011,677 A | 4/1991 | Day et al. | 424/1.1 |
| 5,012,357 A | 4/1991 | Schoeppel et al. | 378/20 |
| 5,163,893 A | 11/1992 | Hara et al. | 600/8 |
| 5,342,283 A | 8/1994 | Good | 376/158 |
| 5,405,309 A | 4/1995 | Carden, Jr. | 600/3 |
| 5,503,614 A | 4/1996 | Liprie | 600/7 |
| 5,713,828 A | 2/1998 | Coniglione | 600/7 |
| 5,728,042 A | 3/1998 | Schwager | 600/3 |
| 5,863,284 A | 1/1999 | Klein | 600/3 |
| 5,997,463 A | * 12/1999 | Cutrer | 600/8 |
| 6,200,258 B1 | 3/2001 | Slater et al. | 600/8 |
| 6,327,490 B1 | * 12/2001 | Spetz | 600/427 |
| 6,440,058 B1 | * 8/2002 | Cutrer | 600/8 |
| 6,482,143 B1 | 11/2002 | Slater et al. | 600/8 |
| 6,503,186 B1 | * 1/2003 | Cutrer | 600/8 |

* cited by examiner

*Primary Examiner*—Eric F. Winakur
(74) *Attorney, Agent, or Firm*—Gordon and Jacobson, P.C.

(57) ABSTRACT

Radioactive therapeutic seeds include a carrier structure bearing a radioactive isotope and a radiopaque marker. According to several embodiments, the seeds include a central plug provided with an axial marker and a relatively transverse bore extending through the marker. A second marker may be positioned in the bore, thereby distinguishing a seed provided with the second marker relative to a seed not provided with the second marker. According to another embodiment, the isotope is deposited on the outer surface of a hollow radiolucent tube. A biologically-compatible, radiolucent, surface-sealing layer seals the external surface of the tube. A radiopaque marker wire of selected length is positioned in the hollow of the tube. Seeds may be distinguished from one another by providing seeds with marker wires of different lengths. According to other embodiments, the seed includes a cylindrical outer member, and an inner member provided within the outer member and having two large diameter portions and a relatively smaller diameter portion therebetween. A marker is disposed within the inner member, and a radioactive isotope is carried on the inner member. The marker may be drilled to a smaller size. Each embodiment permits at least two groups of seeds to be distinguished from one another by the use of differing marker configurations.

15 Claims, 7 Drawing Sheets

RADIOACTIVE THERAPEUTIC SEED HAVING SELECTIVE MARKER CONFIGURATION

This is a continuation of application Ser. No. 09/514,787, filed Feb. 28, 2000, now U.S. Pat. No. 6,487,143 B1 issued Nov. 19, 2002.

This application is a continuation-in-part of U.S. Ser. No. 09/371,243, filed Aug. 10, 1999, which is hereby incorporated by reference herein in its entirety.

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of one or more tiny capsules (seeds) into or around a treatment site. The capsules contain a radioactive isotope that irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they are relatively small, typically approximately 0.025 inch in diameter and approximately 0.16 inch long, so that they may be implanted using minimally invasive instruments and techniques. Second, the radioactive isotope must be enclosed in a biocompatible protective package since the seeds are typically not removed and will remain in the body for many years. Third, the isotope should be positioned within the protective package so as to avoid any "hot spots" of radiation. Fourth, each seed preferably includes a radiopaque (e.g. high Z material) marker so that it can be located at the treatment site with the aid of fluoroscopy. Fifth, the protective package and the radiopaque marker are preferably configured such that each does not cast "shadows" in the irradiation pattern of the isotope.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent describes many of the essential features of radioactive therapeutic seeds. Lawrence describes radioactive isotopes (I-125, Pd-103, Cs-131, Xe-133, and Yt-169) which emit low energy X-rays and which have relatively short half-lives. Once implanted at a treatment site, these isotopes provide sufficient radiotherapy without posing a radiation danger to the medical practitioner (s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which substantially do not absorb X-rays. The isotope is coated on a rod shaped carrier made of similar X-ray transparent (e.g. low Z) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at or around the treatment site.

The Coniglione patent provided a tubular seed adapted for longitudinally receiving suture material to facilitate securing the seed at an implant site. The seed optionally includes a radiopaque band centrally located on the outer surface of the seed, and the radioactive isotope either extends over the entire outer surface of the seed, including over the band, or is coated on the outer surface of the seed from the ends of the seed to areas adjacent the edges of the band.

Despite the fact that radioactive therapeutic seeds have been in use for over thirty years and despite the several significant improvements made in these seeds, many concerns still exist regarding their design. In certain instances where radioactive seed therapy is prescribed for a patient, a physician may desire to have different levels of radioactivity at various locations within the treatment site and thereafter monitor how the tissue is affected by seeds radiating particular levels of radiation. Or the physician may want to implant seeds having isotopes with different half lives, thereby permitting selected locations to receive radiation over a longer period of time, and monitor which seeds are active. However, according to the known seed designs and methodology, it is not possible to distinguish one seed from another after implantation based upon a seed marker with an imaging systems, e.g., X-ray. Due to the indistinguishability of the seeds, implantation of seeds having different respective properties at a single site of treatment is not purposefully performed.

SUMMARY OF THE INVENTION

It is therefore an object of the invention to provide a system of radioactive therapeutic seeds in which at least one of the therapeutic seeds has a different level of radioactivity relative to other seeds.

It is also an object of the invention to provide a system of radioactive therapeutic seeds in which at least one of the therapeutic seeds has a marker which is different relative to other seeds.

It is another object of the invention to provide radioactive therapeutic seeds in which at least one of the therapeutic seeds has a different level of radioactivity and/or different half-life relative to other seeds and the marker in the at least one therapeutic seed indicates the different level of radioactivity and/or half-life relative to the other seeds.

It is an additional object of the invention to provide radioactive therapeutic seeds in which different seeds are provided with markers of different size which indicate their respective levels of radioactivity or half-life.

It is yet another object of the invention to provide a radioactive therapeutic seed which is adapted to receive markers of various lengths by a physician just prior to insertion.

It is yet a further object of the invention to provide a radioactive therapeutic seed which is adapted to have a marker which can be selectively configured by a physician just prior to insertion.

In accord with these objects which will be discussed in detail below, the radioactive therapeutic seeds of the present invention include a carrier structure bearing a radioactive isotope and a radiopaque marker.

According to a first embodiment of the invention, the isotope bearing structure may be one or more radiolucent particles, preferably made from titanium, aluminum or glass, and preferably spherically shaped. The particles are provided with a thin coating of silver to facilitate the adhesion of the isotope thereto. Also provided is a relatively thick tubular titanium plug having an axial first radiopaque marker therein. The plug preferably includes a circumferential ridge against which the open ends of the two halves of the capsule are butt against and welded thereto. The plug and the marker are provided with a transverse bore accessible from the exterior of the seed. A second marker may be positioned in the bore, thereby radiographically distinguishing a seed provided with the second marker relative to a seed not provided with the second marker; i.e., a seed provided with solely the first marker will have a broken linear radiographic image, while a seed provided with both the first and second markers will have a cross-shaped radiographic image. A plurality of seeds as described may be provided in a system which includes a plurality of seeds and a plurality of second markers for selective insertion into the seeds by a physician. Alternatively, the seeds may be provided to the physician already divided into groups which are distinguishably radiographically marked.

According to a second embodiment of the invention, a seed includes an isotope bearing structure, which is preferably a pair of silver tubes having an interior surface on which the isotope is provided. One silver tube is positioned in each half of the capsule, and the halves of the capsule are welded about a relatively thick centrally located tubular titanium plug. The plug is preferably provided with a first radiopaque marker therein. The plug and the marker are provided with a transverse bore accessible from the exterior of the seed, and the bore may be provided with a second marker, as described above. In addition, the isotope bearing tube is preferably smaller than the interior of each half of the capsule, and a spacer is preferably provided in each half of the capsule between the tube and the plug to prevent relative movement of the tube within the capsule.

According to a third embodiment of the invention, the isotope is deposited on the outer surface of a hollow radiolucent tube. A radiopaque band may be centrally located on the outer surface of the seed, and the radioactive isotope may then either extend over the entire outer surface of the seed, including over the band, or may be coated on the outer surface of the seed from the ends of the seed to areas adjacent-the edges of the band. A biologically-compatible, radiolucent, surface-sealing layer seals the external surface of the tube. A radiopaque marker wire is positioned in the hollow of the tube, and where the seed is provided with a radiopaque band, the marker wire is preferably of a length different than the band. It will be appreciated that in a system of seeds according this embodiment, seeds may be radiographically distinguished from one another by providing seeds with marker wires of different lengths.

According to a fourth embodiment of the invention, the seed includes an element on which the isotope is provided, and a marker which can be varied in size or shape by application of energy to the seed.

According to fifth through ninth embodiments of the invention, the seed includes a substantially cylindrical outer member, and a substantially cylindrical inner member provided within the outer member and having two large diameter portions and a relatively smaller diameter portion therebetween. A marker which permits at least one of a radiographic and a MRI image is longitudinally disposed within the inner member, and a radioactive isotope is carried on the small diameter portion of the inner member. In each embodiment, the marker may be drilled to a smaller size, e.g., with a laser drill or mechanical drill, to radiographically distinguish the drilled marker from a non-drilled marker.

Each embodiment permits at least two groups of seeds to be radiographically distinguished from one another by the use of differing marker configurations. Each embodiment is further capable of being selectively marked by the physician prior to implantation of the seeds, or by the manufacturer for delivery to the physician in radiographically distinguishable sets. As a result, seeds having different levels of radiation emission can be distinguished in vivo and their effect monitored by the physician.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
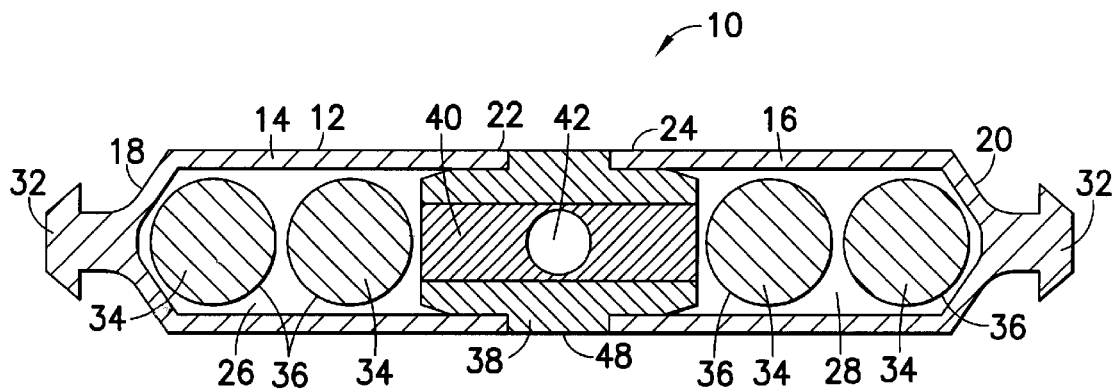
FIG. 1 is an enlarged schematic longitudinal section of a radioactive therapeutic seed according to a first embodiment of the invention.
Figure 2:
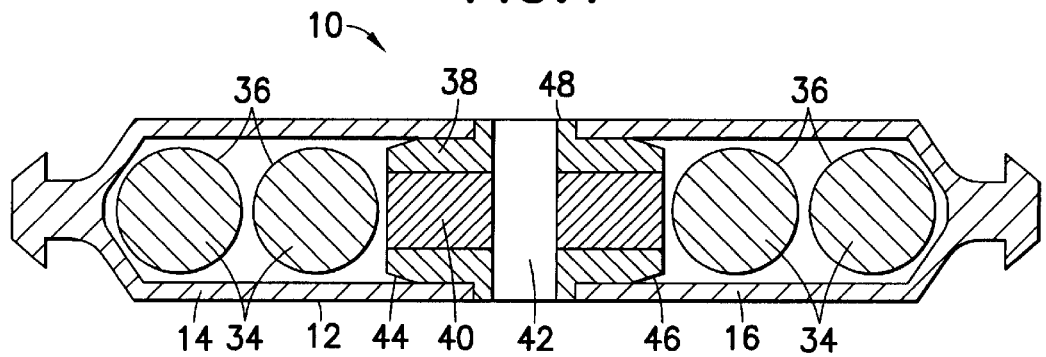
FIG. 2 is a view similar to FIG. 1 with the seed axially rotated by 90° relative to the view shown in FIG. 1.

Referring now to FIGS. 1 and 2, according to a first embodiment of the invention, a radioactive therapeutic seed 10 includes a preferably titanium capsule 12 defined by two halves 14, 16, each having a closed end 18, 20, an open end 22, 24, and an interior portion 26, 28. Each closed end 18, 20 is optionally provided with a connector 32 for connecting to a spacing link (not shown), as described in detail in co-owned U.S. Ser. No. 09/312,215, hereby incorporated by reference herein in its entirety. In the interior portion 26, 28 of each half 14, 16 of the capsule 12, isotope bearing structures 34 are provided. Preferably, the isotope bearing structures 34 are one or more radiolucent particles, preferably made from titanium, aluminum or glass, and preferably spherically shaped. As used herein, the terms "radiotransparent", "radiolucent", "radiotranslucent", and "low Z material" are used interchangeably. The particles 34 are provided with a thin coating of silver over which a radioactive isotope 36 is provided. The two halves 14, 16 of the capsule are welded about a plug 38. The plug 38 is preferably a relatively thick titanium tube. A radiopaque marker 40 is provided axially in the plug 38. Additionally or alternatively, the plug 38 or marker 40 may be comprised of a diamagnetic substance, e.g., a gadolinium metal or salt, to permit visualization of the seed with magnetic resonance imaging (MRI). The plug 38 and preferably the marker 40 are provided with a transverse preferably diametric bore 42 capable of receiving a second radiopaque and/or MRI-visible marker. The plug 38 preferably includes tapered ends 44, 46 to facilitate positioning the open ends 22, 24 thereover, and a central circumferential ridge 48 against which the open ends of the two halves of the capsule are butt against and welded thereto.

Figure 3:
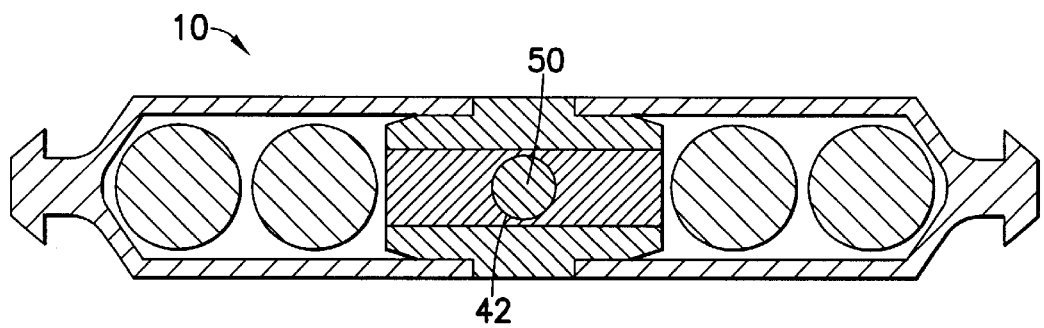
FIG. 3 is a view similar to FIG. 1 with the radioactive therapeutic seed according to a first embodiment of the invention shown with a secondary marker provided therein.
Figure 4:
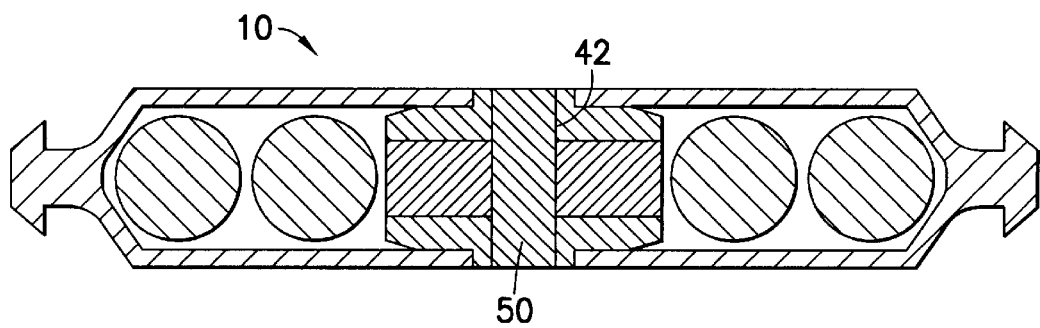
FIG. 4 is a view similar to FIG. 3 with the seed axially rotated by 90° relative to the view shown in FIG. 3.

Turning now to FIGS. 3 and 4, a second radiopaque marker 50 may be positioned in the bore 42 of the seed 10, thereby radiographically distinguishing a seed provided with the second marker relative to a seed not provided with the second marker; that is, a seed provided with solely the first marker 40 will have in one orientation a broken linear radiographic image (FIG. 2), while a seed provided with both the first marker 40 and second marker 50 will have in one orientation a cross-shaped radiographic image (FIG. 4). A system may thereby be provided which includes a plurality of seeds 10 and a plurality of second markers 50 for selective insertion into the seeds by a physician prior to implantation of the seeds into a patient. Alternatively, the seeds may be provided to the physician already divided into groups which are distinguishably radiographically marked; i.e., provided with and without second markers.

Figure 5:
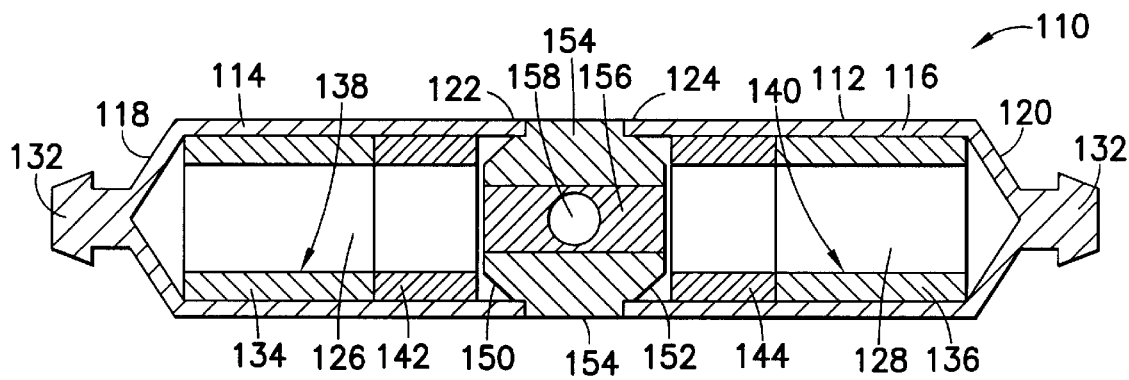
FIG. 5 is an enlarged schematic longitudinal section of a radioactive therapeutic seed according to a second embodiment of the invention.
Figure 6:
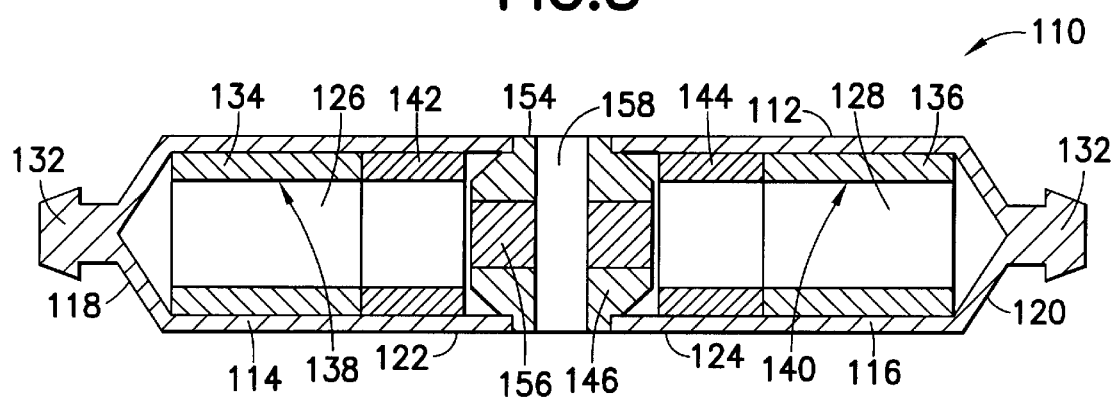
FIG. 6 is a view similar to FIG. 5 shown with the seed axially rotated by 90° relative to the view shown in FIG. 5.
Figure 7:
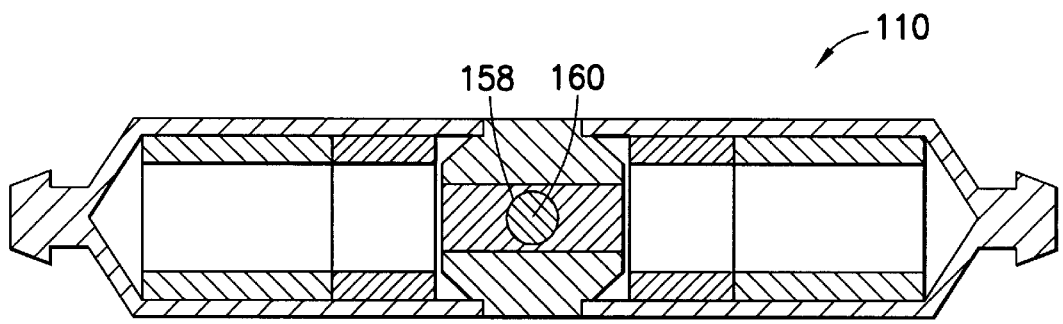
FIG. 7 is a view similar to FIG. 5 with the radioactive therapeutic seed according to a first embodiment of the invention shown with a secondary marker provided therein.
Figure 8:
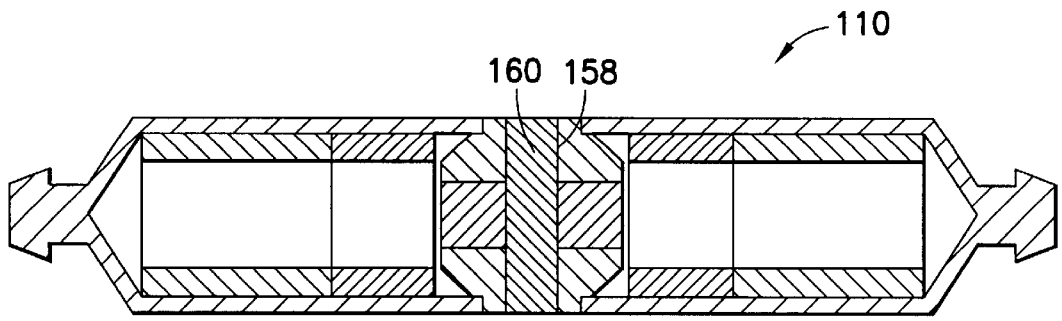
FIG. 8 is a view similar to FIG. 7 shown with the seed axially rotated by 90° relative to the view shown in FIG. 7.

Referring now to FIGS. 5 and 6, a second embodiment of a therapeutic seed 110 according to the invention is shown. The seed 110 includes a radiolucent titanium capsule 112 defined by two halves 114, 116, each having a closed end 118, 120, optionally provided with a connector 132, an open end 122, 124, and an interior portion 126, 128. In the interior portion 126, 128 of each half 114, 116 of the capsule 112, a silver tube 134, 136 is provided. Each tube 134, 136 is preferably 0.025 inch in length and preferably has a wall thickness of 0.004 inch. The interior surfaces 138, 140 of the tubes are coated with I-125 or another radioisotope. As the tubes 134, 136 may be shorter than the length of the interior portion 126, 128, spacers 142, 144 may be provided in the interior portion to prevent relative movement of the tubes within the capsule 112. The two halves 114, 116 of the capsule are welded about a plug 146. The plug 146 is preferably a titanium tube having tapered ends 150, 152 to facilitate positioning the open ends 122, 124 thereover, and a central circumferential ridge 154 against which the open ends of the two halves of the capsule are butt against and welded thereto. A radiopaque marker 156 is provided in the plug 146. Additionally or alternatively, the marker 156 may be MRI-visible. The plug 146 and the marker 156 are provided with a diametric bore 158 accessible from the exterior of the seed 110. Turning now to FIGS. 7 and 8, the bore 158 may be provided with a second marker 160, as described above, to thereby radiographically distinguish seeds provided with and without second markers.

Figure 9:
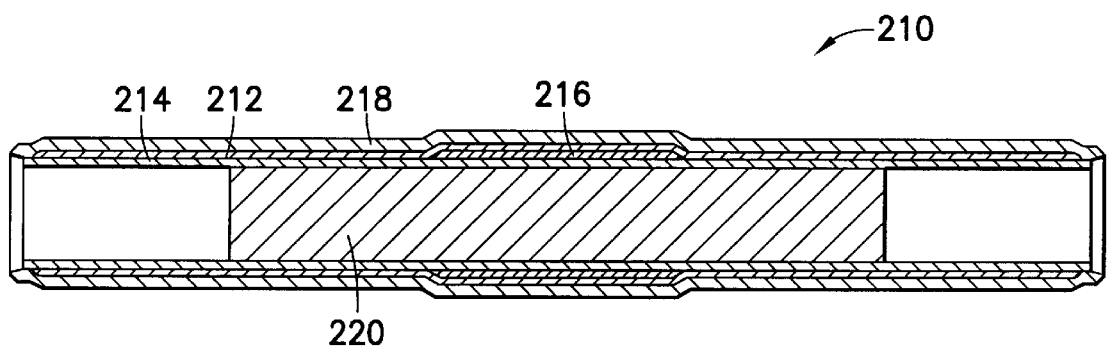
FIG. 9 is an enlarged schematic longitudinal section of a radioactive therapeutic seed according to a third embodiment of the invention shown with a wire marker having a first length.
Figure 10:
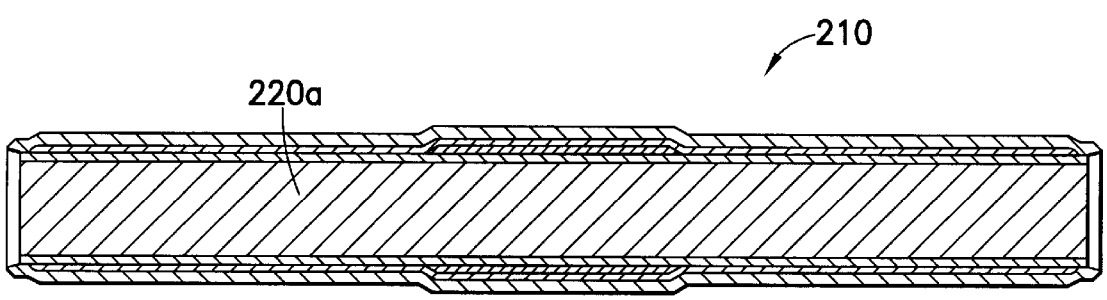
FIG. 10 is a view similar to FIG. 9 shown with a wire marker having a second length different than the first length.

Referring now to FIG. 9, a third embodiment of a radioactive therapeutic seed according to the invention is shown. The seed 210 comprises a radioactive isotope 212 deposited on the outer surface of a hollow radiolucent tube 214. Optionally, a radiopaque band 216 may be centrally located on the outer surface of the tube 214, and the radioactive isotope 212 may then either extend over the entire outer surface of the tube 214, including over the band 216, or may be coated on the outer surface of the seed from the ends of the seed to areas adjacent the edges of the band. A biologically-compatible, radiolucent, surface-sealing layer 218 seals the external surface of the tube 214. The seed as described thus far is substantially similar to that disclosed in U.S. Pat. No. 5,713,828 which is hereby incorporated by reference herein in its entirety. In accord with the invention, a radiopaque marker wire 220 is positioned in the hollow of the tube 214, and where the seed is provided with a radiopaque band 216, the marker wire is preferably of a length different than the band. The length of the marker wire 220 may be selected to provide an indication of the level of radioactivity of the seed 210. For example, referring to FIG. 10, a marker wire 220a relatively longer than marker wire 220 shown in FIG. 9 may be used to radiographically distinguish the seed shown in FIG. 9 from the seed shown in FIG. 10. It will be appreciated that, in accord with this embodiment, a system of seeds may be provided which includes at least two sets of seeds radiographically distinguishable from each other.

Figure 11:
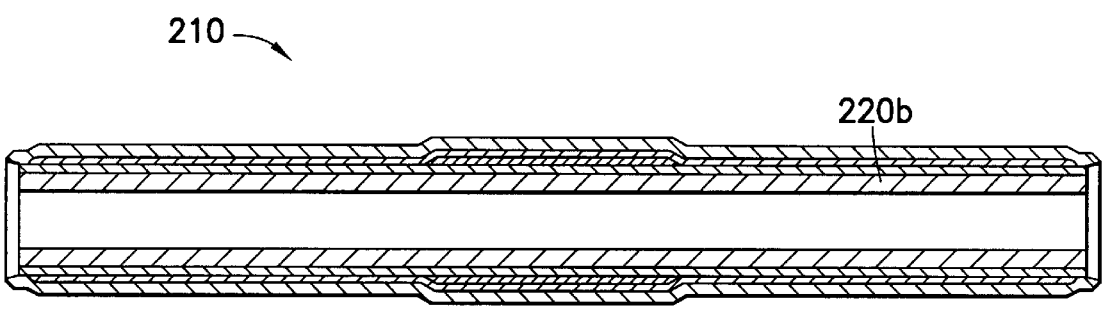
FIG. 11 is a view similar to FIG. 9 shown with two tubular co-axial markers.

With respect to the third embodiment, it will be appreciated that the marker wire may alternatively be a tubular marker 220b, thereby permitting the passage of a suture wire therethrough to couple the seed to the tissue at an implant site (FIG. 11). It will be further appreciated that multiple markers may be provided in the hollow of the tube, e.g., a tubular marker and a marker wire extending through the tubular marker. Additionally, transverse or diametric holes may be provided in the tube, and the marker wire may be positioned within with holes; i.e., the orientation of the second markers in the first and second embodiments. Furthermore, radiolucent plugs may be provided on either end of the marker wire or tubular marker to seal the seed about the markers.

Figure 12:
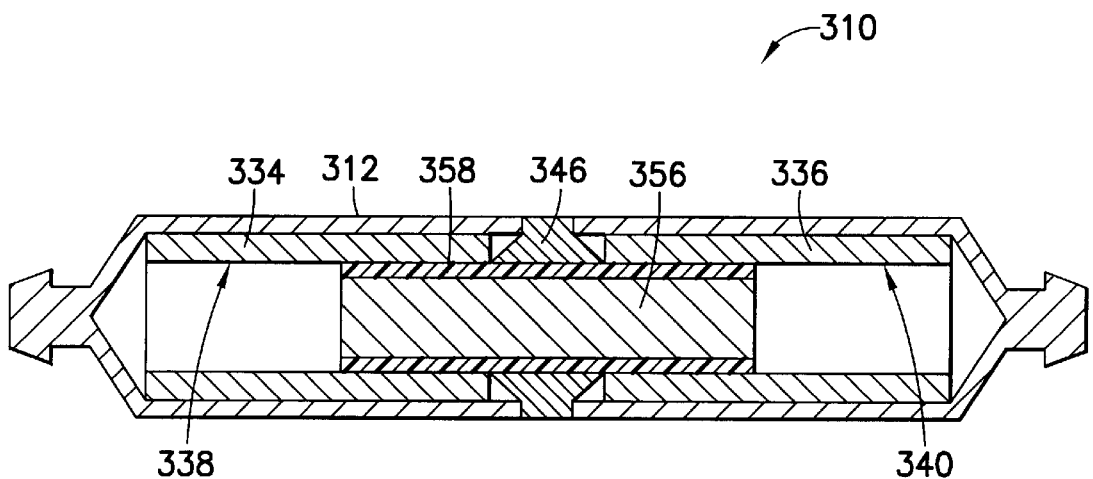
FIG. 12 is an enlarged schematic longitudinal section of a radioactive therapeutic seed according to a fourth embodiment of the invention shown with a marker having a first shape.
Figure 13:
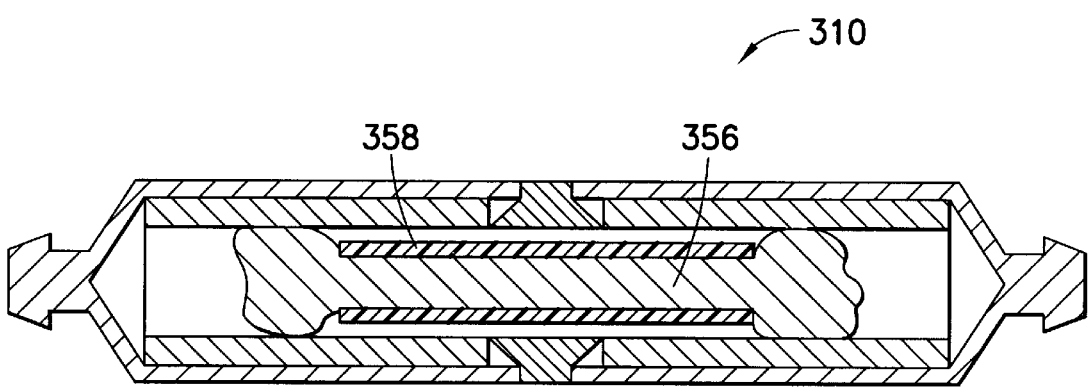
FIG. 13 is a view similar to FIG. 12 with the marker having a second shape.

Turning now to FIG. 12, a fourth embodiment of a therapeutic seed 310 according to the invention is shown. The seed 310, substantially as described with respect to the second embodiment, includes a radiolucent titanium capsule 312 welded about a plug 346, and one or more tubes 334, 336 within the capsule having I-125 or another radioisotope coated on the interior surfaces 338, 340 of the tubes. A radiopaque marker 356 is provided within the capsule. According to the fourth embodiment, the marker is a radiopaque material having a low melting point, e.g., an indium alloy, a bismuth alloy, or a solder or other eutectic, which is in solid form when the seed 310 is at body temperature. A heat-shrinkable or elastic sleeve 358 may be provided over the marker. Referring to FIG. 13, when heat is applied to the seed 310, such that the seed is at a temperature greater than body temperature, the radiopaque material of the marker 356 melts and the sleeve 358 shrinks about the melted material, forcing at least some of the radiopaque material from the sleeve such that the marker 356 changes shape, e.g., forms a relatively longer bar-bell shape.

It will be appreciated that in the fourth embodiment, otherwise like seeds which were made at different times, and therefore have different remaining useful life through which they may provide a therapeutic dose of radiation, may be separately identified and used together. For example, heat may be applied to a first set of relatively older seeds to cause their markers to be relatively longer than a second set of relatively newer seeds. Once implanted, the position of the seeds may be individually monitored by distinguishing their respective markers.

Figure 14:
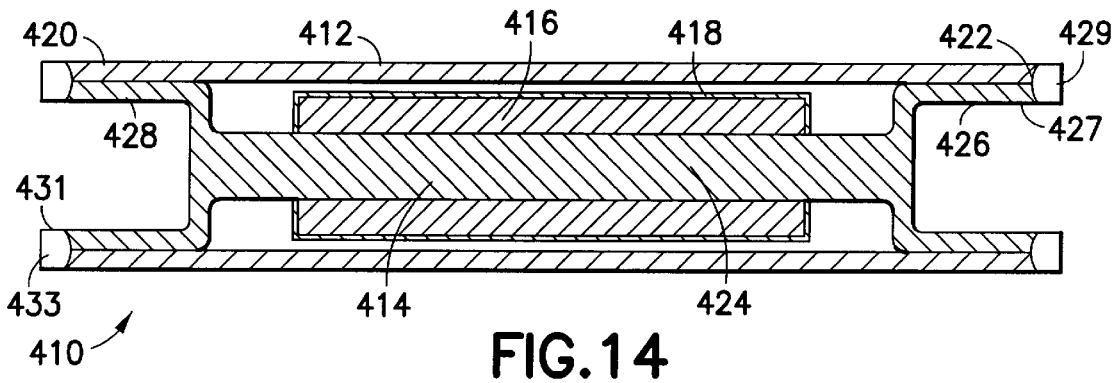
FIG. 14 is an enlarged schematic longitudinal section of a radioactive therapeutic seed which is thereafter modified in accord with the fifth embodiment of the invention.

Referring now to FIG. 14, a seed 410 used in the manufacture of a fifth embodiment of the invention is shown. The seed 410 includes an outer cylinder 412, a stepped inner cylinder (or inner device) 414, a band or carrier 416, and a radioactive isotope 418 coated on the carrier 416 about a portion of the stepped inner cylinder. The outer cylinder 412 and the inner cylinder 414 are made of radiotransparent, radiotranslucent, or low Z material which does not absorb much radiation. The outer cylinder 412 has a substantially constant diameter, a closed end 420, and an open end 422. The stepped inner cylinder 414 has a reduced diameter portion 424 and an enlarged diameter portion 426. The band or carrier 416 is applied over the reduced diameter portion 424 such that the stepped inner cylinder 414 carries the band, as shown in FIG. 14. For example, the band or carrier 416 may be a resilient plastic band which includes a peripheral longitudinal slot (not shown) enabling the band to be opened and placed over the reduced diameter portion. As another example, the band 416 may be made from a deformable and preferably radiotransparent metal which may be bent about the reduced diameter portion 424 such that the band cannot be inadvertently released from the inner cylinder 414. Alternatively, the radioisotope may be coated directly on the reduced diameter portion 424 of the stepped inner cylinder 414, with the cylinder acting as a carrier for the radioisotope.

As shown in FIG. 14, the enlarged diameter portion 426 of the inner cylinder 414 has an outer diameter which is substantially the same as the inner diameter of the open end of the outer cylinder 412. The seed 410 is sealed by placing the stepped inner cylinder 414 inside the outer cylinder 412 so that the enlarged diameter portion 426 of the inner cylinder 414 engages with the open end 422 of the outer cylinder 412 as shown. The end 427 of the enlarged diameter portion 426 of the inner cylinder 414 is welded to the open end 422 of the outer cylinder 412 as indicated by reference numeral 429. Likewise, the end 431 of the enlarged diameter portion 428 of the inner cylinder 414 is welded to the open end 420 of the outer cylinder 412 as indicated by reference numeral 433. The wall thickness of the outer cylinder 412 is substantially constant and the enlarged diameter portion 426 of the inner cylinder 414 is preferably hollow with a wall thickness comparable to the wall thickness of the outer cylinder. The relative sizes of the outer and inner cylinders facilitate assembly of the seed 410 and permit a substantially isotropic radiation pattern.

Figure 15:
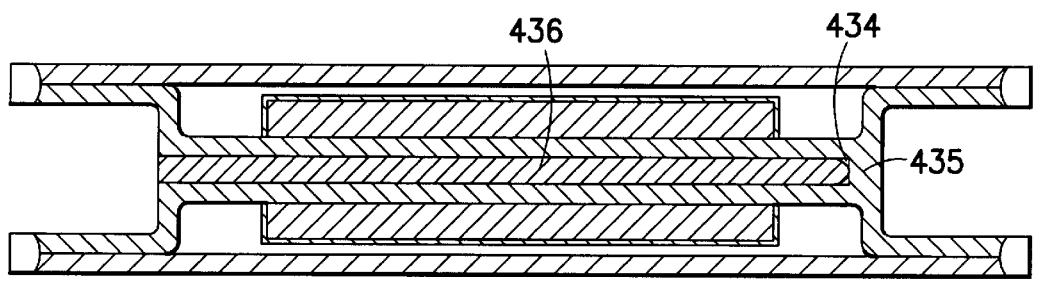
FIG. 15 is a view similar to FIG. 14 in which the seed of FIG. 14 is modified by providing a longitudinal bore therein and a marker in the bore according to the fifth embodiment of the invention.

Referring to FIG. 15, once the seed 410 is formed, a longitudinal bore 434 is provided in the seed from one end of the seed, but does not create a throughbore; i.e., the bore 434 does not extend completely through the seed as the bore has a closed end 435. The bore 434 may be made by laser drilling, mechanical drilling or boring, or other means. A radiopaque marker 436 is then positioned in the bore 434, preferably substantially completely filling the bore.

Figure 16:
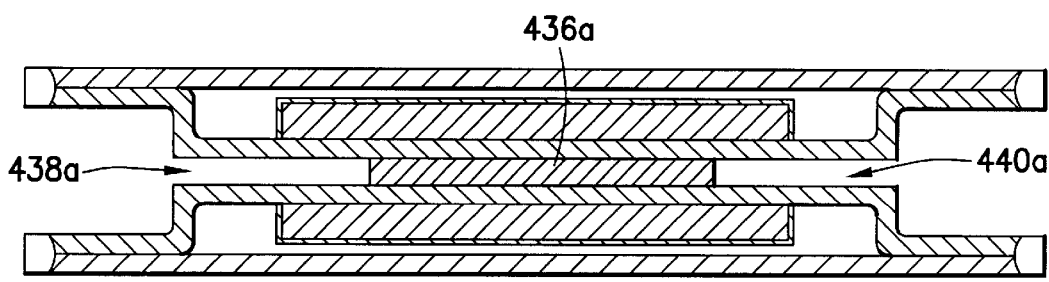
FIG. 16 is a view similar to FIG. 15 in which the marker has been altered in size to indicate a differing level of radioactivity of the seed relative to a marker unaltered in size.

Then, referring to FIG. 16, when it is necessary to distinguish a seed having one level of radioactivity from a seed having another level of radioactivity, a portion of the marker 436a of seed 410a may be removed by drilling the marker down to a smaller size. Preferably, the marker 436a is drilled through both its ends 438a, 440a (and through the closed end of the bore) such that the remaining portion of the marker 436a is longitudinally centrally located within the bore to maintain a uniform radiation distribution pattern. Preferably, a seed with a relatively lower radioactivity is provided with the marker of relatively smaller size. The seeds are thereby easily distinguishable under fluoroscopy.

Figure 17:
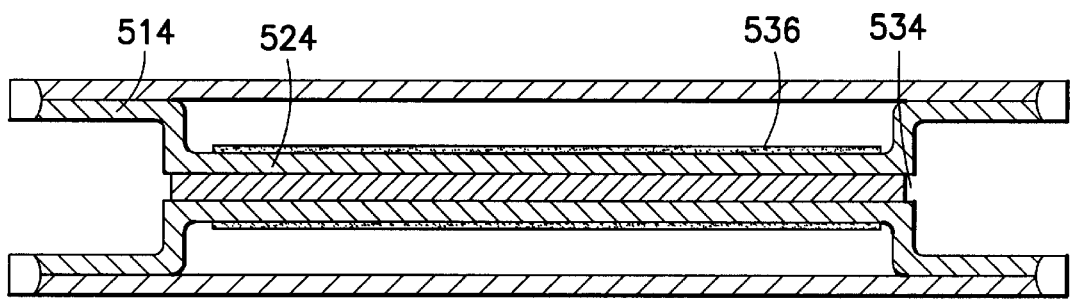
FIG. 17 is a view similar to FIG. 15 in which the seed is provided with a lumen and marker therein according to a sixth embodiment of the invention.

Turning now to FIG. 17, a sixth embodiment of a brachytherapy seed 510 according to the invention, substantially similarly to the fifth embodiment (with like parts given numbers incremented by 100) is shown. The radioisotope is provided as a coating directly on the reduced diameter portion 524 of the stepped inner cylinder 514 (or inner device), and the seed is formed as an encapsulation as described above. Then, a longitudinal throughbore 534 is provided completely through the seed. The throughbore 534 may be made by laser drilling, mechanical drilling or boring, or other means. A radiopaque marker 536 is then positioned in the bore 534, preferably substantially completely filling the bore. The marker 536 may then be reduced in size by drilling the marker, preferably equal amounts from each end.

Figure 18:
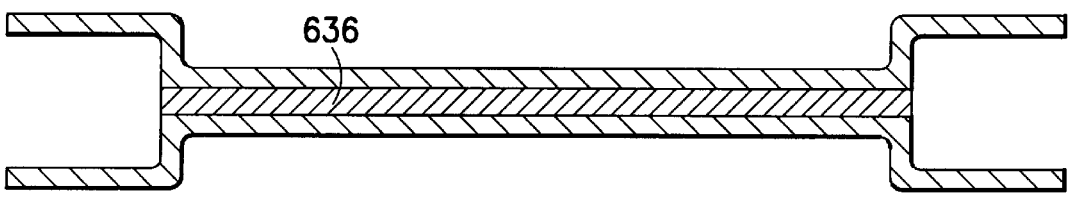
FIG. 18 is an enlarged schematic longitudinal section of a first manufactured portion of a radioactive therapeutic seed according to a seventh embodiment of the invention.
Figure 19:
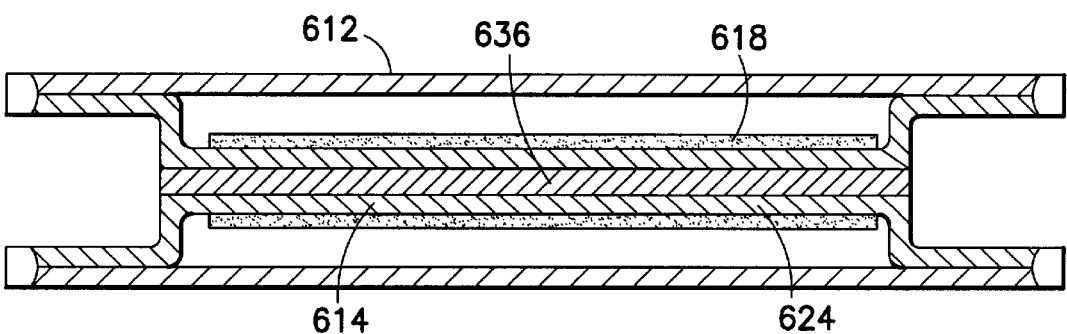
FIG. 19 is an enlarged schematic longitudinal section of a radioactive therapeutic seed according to the seventh embodiment shown with a marker of a first length.

Referring now to FIGS. 18 and 19, a seed substantially as described above with respect to the sixth embodiment is manufactured in a different manner according to a seventh embodiment of the invention. First, a stepped inner cylinder 614 having a central reduced diameter portion 624 is provided with a longitudinal throughbore 634. A radiopaque marker 636 is provided in the throughbore 634 (as shown in FIG. 18). Alternatively, the inner cylinder is formed about the marker, for example, by bending a suitable material about the marker to form the inner cylinder. Next, the reduced diameter portion 624 of the inner cylinder 614 is coated or otherwise provided with the radioisotope 618. Then, referring particularly to FIG. 19, the outer cylinder 612 is provided about the inner cylinder 614 and the ends of the inner and outer cylinders are sealed together, e.g., by welding, to form the seed encapsulation 610. The marker 636 of the seed 610 may then be longitudinally drilled, preferably at each end of the seed (as described above with respect to FIG. 16), to remove equal amounts of the marker and thereby reduce the size of the marker.

Figure 20:
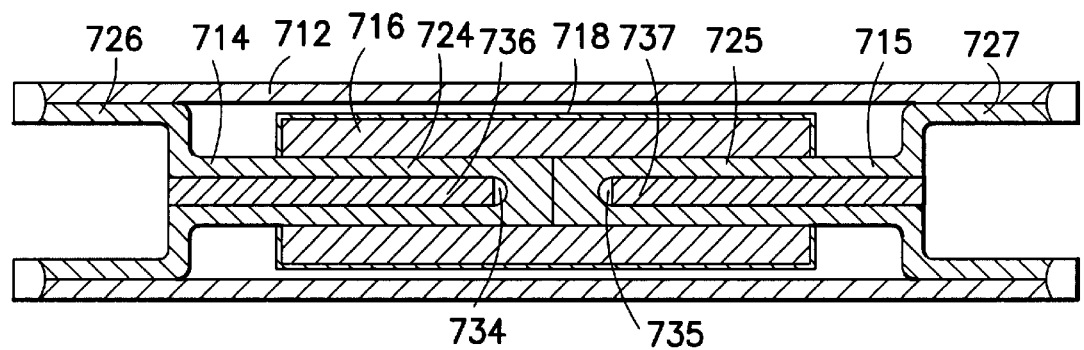
FIG. 20 is an enlarged schematic longitudinal section of a radioactive therapeutic seed according to an eighth embodiment shown with markers of a first length.
Figure 21:
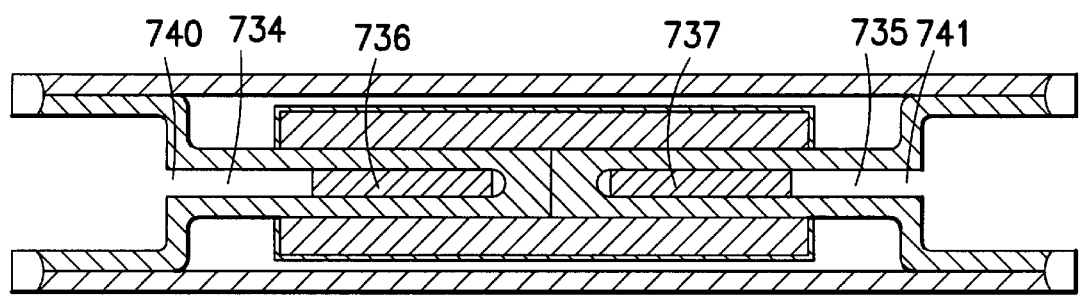
FIG. 21 is a view similar to FIG. 20 in which the markers are drilled down to a second length.

Turning now to FIG. 20, a seed 710 according to an eighth embodiment of the invention is shown. The seed 710 includes an outer cylinder 712, first and second stepped inner members 714, 715 (together forming an inner device) each having a reduced diameter portion 724, 725 and an enlarged diameter portion 726, 727, markers 736, 737, a band or carrier 716, and a radioactive isotope 718 carried by the band 716 about the reduced diameter portions of the stepped inner members 714, 715. The inner members 714, 715 include externally directed bores 734, 735, and the markers 736, 737 are provided in the bores 734, 735. The outer cylinder 712 and the inner portions 714, 715 are made of a low Z material which does not absorb much radiation. The radioisotope 718 is preferably provided on a cylindrical band 716, and the reduced diameter portions 724, 725 of the stepped inner members 714, 715 are inserted into opposite ends of the band 716. Alternatively, the radioisotope may be coated directly on the reduced diameter portions 724, 725 of the stepped inner members 714, 715 (inner device). The seed 710 is sealed by placing the stepped inner members 714, 715 inside the outer cylinder 712 so that the enlarged diameter portion 726, 727 of the inner members 714, 715 engage with the open ends 722, 723 of the outer cylinder 712, and are welded together. The markers 736, 737 may be altered in size by longitudinally drilling the markers at 740, 741 and into the bores 734, 735 as described above and as shown in FIG. 21.

Figure 22:
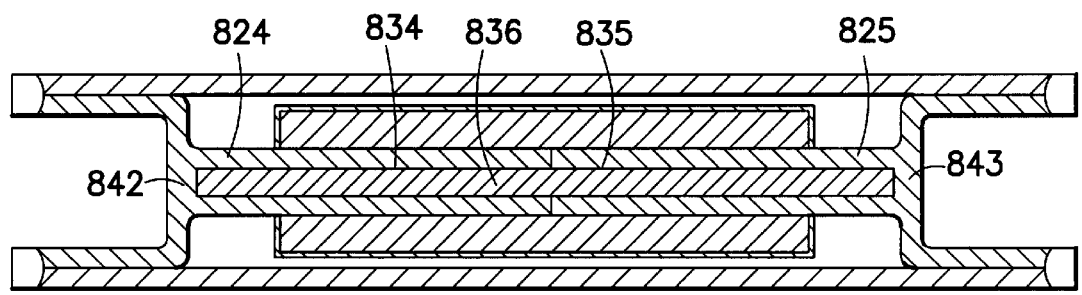
FIG. 22 is an enlarged schematic longitudinal section of a radioactive therapeutic seed according to a ninth embodiment shown with a marker of a first length.

Referring now to FIG. 22, a seed 810 according to a ninth embodiment of the invention and substantially similar to the eighth embodiment (with like parts having numbers incremented by 100 relative thereto) is shown. The distinguishing feature relative to the eighth embodiment is that each stepped inner member 824, 825 includes a medially directed bore 834, 835 and preferably a single marker 836 extends within the bores. The marker 836 of the seed may altered in size by drilling through the closed ends 842, 843 of the inner member, into the bores 834, 835 and into the marker 836.

Each embodiment permits at least two groups of seeds to be radiographically distinguished from one another by the use of differing marker configurations. Each embodiment is further capable of being selectively configured by the physician prior to implantation of the seeds, or by the manufacturer for delivery to the physician in radiographically distinguishable sets. As a result, seeds having different levels of radiation emission can be distinguished in vivo and their effect monitored by the physician. This is particularly useful in that the invention permits discrete monitoring of two or more sets of seeds, e.g., seeds having relatively different levels of radiation, seeds having relatively different radiation distribution, or seeds having radioactive isotopes with relatively different half-lives, as each set may be radiographically distinct. In addition, it will be appreciated that the provision of a second marker to each embodiment does not detrimentally affect the relatively isotropic distribution of the seeds.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. It will be appreciated that numerous other seed designs may be configured to receive a secondary marker or to permit marker alteration to thereby permit relative seed differentiation, and that the particular designs disclosed herein are only exemplary. In addition, while the second marker, in the first and second embodiments, the marker wire in the third embodiment, or the markers in the fourth through ninth embodiments, have been described as being radiopaque, it will be appreciated that such markers may be MRI-visible. Likewise, while the first marker or marker band has been described as being radiopaque, each may be MRI-visible, and the second marker and marker wire may be radiopaque. Also, while the second marker in the first and second embodiments has been described as preferably being diametrically and/or transversely oriented, it will be appreciated that the second marker need only be angled relative to the first marker or non-axial relative to the longitudinal axis of the capsule. In addition, the wire marker in the third embodiment may be cylindrical or an elongate rectangular shape, each being substantially a wire at the scale of brachytherapy seeds. Furthermore, while capsules in particular embodiments are preferably formed from two halves (for purposes of isotropic radiation distribution), it will be appreciated that the two parts forming the capsule need not be halves, e.g., one part being one third the length of the capsule and the other part begin two thirds the length of the capsule. Moreover, while in embodiments one through four, the isotope bearing surface has been disclosed as the outer surface in particular embodiments and the inner surface in other embodiments, it will be appreciated that either of the inner and outer surfaces may be used as the isotope bearing surface, though it is believed that the embodiments as described provide the most isotropic radiation distribution. In addition, while a particular seed has been disclosed having a marker which changes shape when energy is applied to the seed, it will be appreciated that such markers may be used in seeds having different radioisotope bearing elements and different capsule configurations. Also while a meltable marker has been described having a heat shrinkable or elastic sleeve thereabout, it will be appreciated that the sleeve is not required, and that the marker can be altered from a defined shape, e.g., cylindrical, to an amorphous configuration upon melting. Further, where a sleeve is used, it will be appreciated that the marker after heating, if substantially melted, may take the configuration of two or more separated masses. In addition, while in the fifth through ninth embodiments, markers having an outer diameter substantially the same size as the inner diameter of bore are shown, it will be appreciated that markers of a relatively smaller diameter may be used and that the open end or ends of the bore may be capped to retain the marker. Furthermore, in the fifth through ninth embodiments, while marker size reduction is disclosed, it will be appreciated that a first marker having a length substantially half that of the bore may be centrally provided within the bore, and then a second marker of substantially the same size may be inserted into the bore to slide over the first marker and substantially completely fill the bore to thereby distinguish the seed with an imaging device. It will therefore be appreciated by those skilled in the art that yet other modifications could be made to the provided invention without deviating from its spirit and scope as claimed.

What is claimed is:

1. A radioactive therapeutic seed system, comprising:
a plurality of radioactive therapeutic seeds, wherein different seeds are provided with markers of different size which indicate their respective levels of radioactivity or half-life.

2. The system according to claim 1, wherein:
at least one of said seeds has a marker which can be selectively configured by a physician just prior to insertion.

3. A radioactive therapeutic seed system, comprising:
a plurality of therapeutic seeds, and
a plurality of markers of various lengths, wherein
at least one of said seeds is adapted to receive markers of various lengths by a physician just prior to insertion.

4. The system according to claim 3, wherein:
at least one of the therapeutic seeds has a different level of radioactivity and/or different half-life relative to other seeds and the marker in the at least one therapeutic seed indicates the different level of radioactivity and/or half-life relative to the other seeds.

5. The system according to claim 3, wherein:
different seeds are provided with markers of different size which indicate their respective levels of radioactivity or half-life.

6. The system according to claim 3, wherein:
at least one of said seeds has a marker which can be selectively configured by a physician lust prior to insertion.

7. A radioactive therapeutic seed system, comprising:
a plurality of therapeutic seeds, wherein different seeds are provided with markers of different size which indicate their respective levels of radioactivity or half-life.

8. The system according to claim 7, further comprising a plurality of markers of various lengths, wherein
at least one of said seeds is adapted to receive markers of various lengths from a physician just prior to insertion of the seed into a patient.

9. The system according to claim 7, wherein:
at least one of said seeds has a marker which can be selectively configured by a physician lust prior to insertion of the seed into a patient.

10. A radioactive therapeutic seed system, comprising:
a plurality of therapeutic seeds, wherein
at least one of said seeds has a marker which can be selectively configured by a physician just prior to insertion of the seed into a patient.

11. The system according to claim 10, further comprising a plurality of markers of various lengths, wherein
at least one of said seeds is adapted to receive markers of various lengths from a physician just prior to insertion of the seed into a patient.

12. The system according to claim 10, wherein:
different seeds are provided with markers of different size which indicate their respective levels of radioactivity or half-life.

13. A radioactive therapeutic seed system, comprising:
a plurality of therapeutic seeds; and
a plurality of markers of various length, wherein
at least one of said seeds is adapted to receive markers of various lengths from a physician just prior to insertion of the seed into a patient.

14. The system according to claim 13, wherein:
at least one of said seeds has a marker which can be selectively configured by a physician lust prior to insertion of the seed into a patient.

15. A method of radioactive seed therapy, comprising:
selecting a radioactive seed;
selecting a marker from a plurality of markers of different length;
inserting the selected marker into the selected seed just prior to insertion of the seed into a patient.

* * * * *

UNITED STATES PATENT AND TRADEMARK OFFICE
CERTIFICATE OF CORRECTION

| | |
|---|---|
| PATENT NO. | : 6,712,752 B2 |
| APPLICATION NO. | : 10/295658 |
| DATED | : March 30, 2004 |
| INVENTOR(S) | : Charles R. Slater et al. |

It is certified that error appears in the above-identified patent and that said Letters Patent is hereby corrected as shown below:

Column 11,
Line 3, "lust" should be replaced with -- just --.

Column 12,
Line 3, "lust" should be replaced with -- just -- (both occurrences).

Signed and Sealed this

Twenty-seventh Day of June, 2006

JON W. DUDAS
*Director of the United States Patent and Trademark Office*